United States Patent [19]
Gilljam et al.

[11] Patent Number: 5,405,372
[45] Date of Patent: Apr. 11, 1995

[54] MEDICAL ELECTRODE ARRANGEMENT

[75] Inventors: Nina Gilljam, Farsta; Heinz Neubauer, Jaerfaella; Jakub Hirschberg, Taeby, all of Sweden

[73] Assignee: Siemens-Elema AB, Solna, Sweden

[21] Appl. No.: 63,568

[22] Filed: May 19, 1993

[30] Foreign Application Priority Data

May 21, 1992 [SE] Sweden .................. 9201601

[51] Int. Cl.$^6$ ............................. A61N 1/04
[52] U.S. Cl. ..................... 607/115; 607/119
[58] Field of Search ............ 128/642; 604/21, 27, 604/53; 607/119, 122, 123, 125–128, 132, 115–117, 133, 148, 156, 96, 98, 99, 103, 105, 106, 113, 129, 130; 606/32; 174/1, 71 R, 68.1, DIG. 12; 336/195, 225; 439/121, 210, 245, 448, 909

[56] References Cited

U.S. PATENT DOCUMENTS

| | | | |
|---|---|---|---|
| 4,026,303 | 5/1977 | Babotai | 607/127 |
| 4,360,031 | 11/1982 | White | 607/120 |
| 4,508,419 | 4/1985 | Galindo | 128/642 |
| 4,953,564 | 9/1990 | Berthelsen | 128/642 |
| 5,105,826 | 4/1992 | Smits et al. | 128/642 |

FOREIGN PATENT DOCUMENTS

| | | | |
|---|---|---|---|
| 1332217 | 12/1963 | France | 174/DIG. 12 |
| 3718324 | 12/1988 | Germany | 607/119 |
| 9113592 | 9/1991 | WIPO | 606/32 |

*Primary Examiner*—William E. Kamm
*Assistant Examiner*—Marianne Parker
*Attorney, Agent, or Firm*—Hill, Steadman & Simpson

[57] ABSTRACT

An electrode arrangement has at least two coiled electrode conductors which are mechanically and electrically interconnected in a contact region. Within the contact region, the flights of the coiled conductors are engaged, such as by the flights of one conductor surrounding the flights of the other conductor, or the flights being intertwined, thereby producing the necessary mechanical and electrical connection by means of the spring force associated with the coiled structure of each conductor. The connection of the conductors thereby becomes simpler to assemble, and does not require crimping, and results in a more reliable and flexible connection area.

6 Claims, 2 Drawing Sheets

MEDICAL ELECTRODE ARRANGEMENT

BACKGROUND OF THE INVENTION

1. Field of the Invention

The present invention relates to an electrode device for a medical apparatus for stimulating living tissue with electrical impulses, of the type having at least two coiled conductors which are electrically and mechanically interconnected in a contact area.

2. Description of the Prior Art

A medical electrode is disclosed in U.S. Pat. No. 4,817,634 which has two coiled conductors which are mechanically and electrically interconnected in a contact area. The document describes a defibrillation electrode comprising an electrode catheter in which a first coiled electrode conductor runs, and an electrode carrier on which a second coiled electrode conductor is arranged in a specific pattern. One end of each electrode conductor is inserted into a coupling sleeve which is crimped onto the ends to electrically and mechanically interconnect the two electrode conductors. The defibrillator electrode is designed for implantation in the heart of a patient.

In an alternative version, of this known device, a plurality of electrode conductors are arranged in simple, closed loops on the electrode carrier. All the conductors are mechanically and electrically coupled in the coupling sleeve.

Coupling conductors with a coupling sleeve have certain disadvantages. In assembly, crimping of the coupling sleeve must be firm enough to prevent detachment of any conductor, which would break the electrical connection. The crimping, however, must not be too forceful, since it might then damage the conductors. When a plurality of conductors is to be interconnected, there is a risk of one of the connections being defective. Since the aforementioned known electrode device is to stimulate the heart, it is exposed to constant, dynamic loading. The contact area is therefore subjected to a large number of load changes which could cause conductor fatigue in the attachment area, since the coupling sleeve is completely inflexible but the conductors are flexible. The conductors are also connected in a contact sleeve which restricts the design of the specific pattern in which the conductors are arranged. If more than one contact sleeve were used when a plurality of conductors is arranged on the electrode carrier, the entire defibrillation electrode would be stiff and obstruct the heart's movements. Moreover, coupling cannot be disengaged, and the number of parts required for assembly of the electrode device increases.

SUMMARY OF THE INVENTION

An object of the present invention is to produce an electrode, having at least two called conductors in which interconnection of the conductors is mechanically and electrically reliable, elastic and resilient, and wherein fewer assembly items are required and the conductors are not damaged, either in assembly or after long-term use.

The above object is achieved in accordance with the principles of the present invention in an electrode device wherein the flights of the respective conductors in the contact area are engaged with each other so that the spring force resulting from the coiled structure of the individual conductors forms the electrical and mechanical interconnection.

Since the conductors are engaged by being coiled around or intertwined with each other, the spring force will hold the conductors together so sufficient mechanical and electrical contact is obtained without any reduction in the flexibility of conductors in the contact area. This increases the possibility of varying the design of the electrode device, since couplings can be made anywhere. A plurality of coupling points on the electrode device itself is then possible without the contact areas becoming stiff or bulky. The contact interface between the two conductors can be made long, since no flexibility is lost, and contact between conductors will be intense when the spring constant is high, since spring force presses the conductors together. As a result, electrical resistance between the two conductors decreases. No additional assembly items are required, and the conductors are left completely intact.

In an embodiment of the electrode device in accordance with the invention, the electrode device is a defibrillation electrode with an electrode carrier, on which at least one of the coiled conductors is arranged in a predetermined pattern to form an electrode surface through which electrical pulses are transmitted to the living tissue, and having an electrode catheter in which the other coiled conductor is provided.

Such an electrode device can be applied directly to the heart or subcutaneously at a given distance from the heart. The contact area is flexible and resilient.

In connection with this embodiment, additional advantages for the defibrillation electrode are obtained if at least two coiled conductors are arranged in predetermined patterns on the electrode carrier, and the two conductors are interconnected in at least one further contact area, which is separated from the contact area between the conductors in the electrode catheter and at least one of the conductors on the electrode carrier.

In this manner, the conductors can be interconnected anywhere on the electrode carrier without the defibrillation electrode losing any flexibility. This is particularly important in cases in which the electrode is applied directly to the heart. In addition, the electrode conductors in this embodiment can be arranged so that distribution of current in the electrode surface is optimized, and the effects of a broken conductor in the defibrillation electrode are minimized.

In another embodiment of the electrode device according to the invention, the electrode device contains at least one symmetrical lead, one of the coiled conductors is provided inside the lead, and a second coiled conductor is provided inside the electrode catheter.

Discharge of the electrical lead's pulses is desirable in, for example, electrode devices for defibrillating a heart when an electrical pulse must be emitted simultaneously across cardiac tissue from one electrode surface to two other electrode surfaces located at a distance from one another, and which are electrically connected to one another via the lead. It is then important for the electrode conductor to retain its flexibility even at the branching point, which is made possible, according to the invention, by intertwining of the coiled conductors. Only one connection contact with the defibrillator is needed for the two electrode surfaces.

In this context, it is an advantage to devise the electrode so it has a detachable adapter device, with an electrode catheter with a connection contact jack at one end, and a symmetrical, branched lead with first and second contact fixtures at its respective free ends, one of the coiled conductors being provided inside the lead and one of the other coiled conductors being provided inside the electrode catheter.

Construction of the contact fixture makes possible a number of different versions of the electrode device with only a small number of parts.

Preferably, the coiled conductors have the same diameter.

DESCRIPTION OF THE PREFERRED EMBODIMENTS

Figure 1:
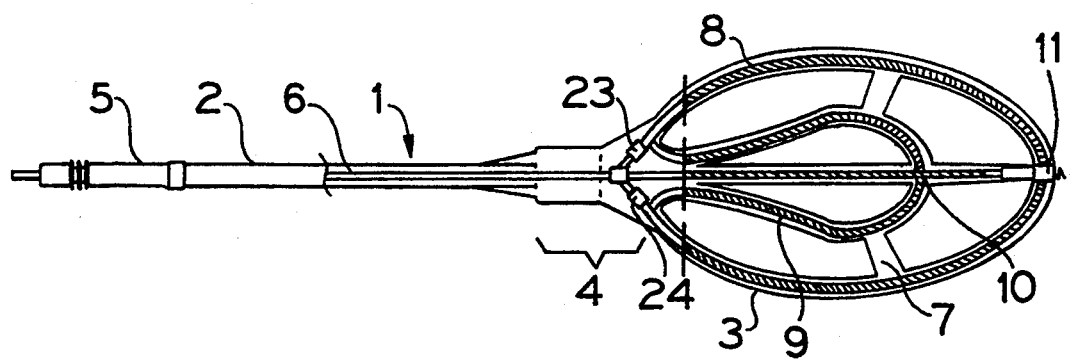
FIG. 1 is a plan view, partly cut away, of a first embodiment of an electrode device constructed in accordance with the principles of the present invention.

FIG. 1 illustrates an electrode device 1 having an electrode catheter 2 and an electrode 3 which are connected to one another in a contact area 4. At its free, proximal end, the electrode catheter 2 has a connection contact 5 for coupling the electrode device 1 to a stimulation pulse generator (not shown), such as a defibrillator. A first coiled electrode conductor 6 runs inside the electrode catheter 2. The first electrode conductor 6 runs through the entire contact area 4 and, as an extension of the electrode catheter 2, out onto an electrode carrier 7 to the defibrillation electrode 3, to the distal end of the defibrillation electrode 3.

In the contact area 4 there is a second spiral electrode conductor 8 which is connected to the first electrode conductor 6. The second electrode conductor 8 runs in an arc along the periphery of the electrode carrier 7 in a closed loop back to the contact area 4. A third spiral electrode conductors 9 runs across the electrode carrier 7 and is connected to the second electrode conductor 8 in two opposite contact areas 23 and 24 on the electrode carrier 7.

Figure 2:
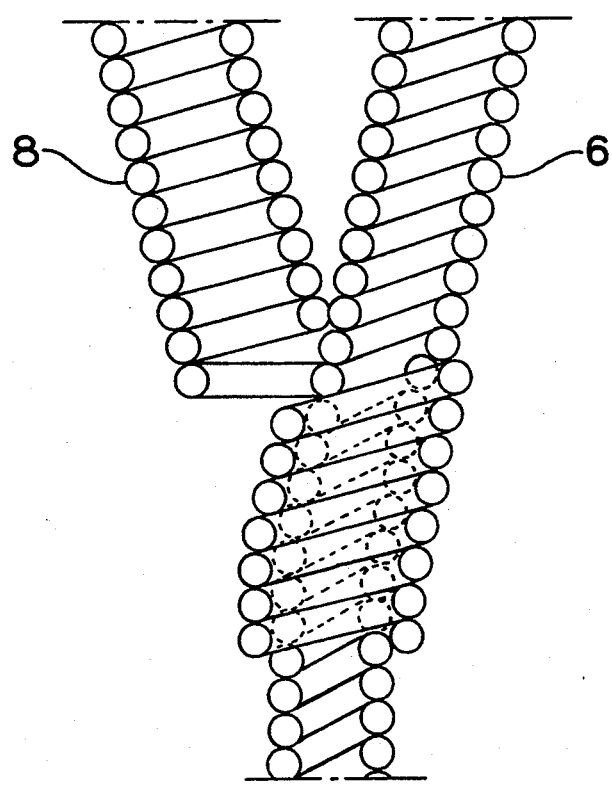
FIG. 2 illustrates a coupling of two electrode conductors in the electrode device according to FIG. 1.

FIG. 2 illustrates how the first electrode conductor 6 is connected to the second electrode conductor 8 by enclosure of a region of the first electrode conductor 6 by the flights of the second electrode conductor 8. The spring force in the second electrode conductor 8, as a result of its coiled structure, achieves sufficient mechanical and electrical coupling. The second electrode conductor 8 and the third electrode conductor 9 are interconnected in the corresponding matter in the contact areas 23 and 24.

In addition to the coupling area between the respective electrode conductors 6, 8 and 9, both the second electrode conductor 8 and the third electrode conductor 9 are in electrical contact with the first electrode conductor 6 at the respective conductor intersection 10 and 11 on the electrode carrier 7.

Figure 3:
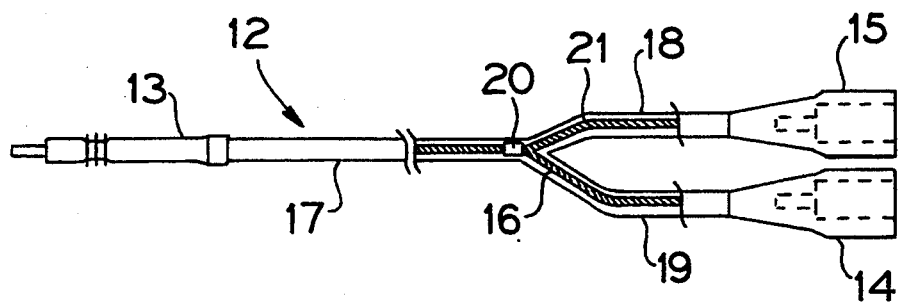
FIG. 3 is a plan view, partly cut away, of an adapter device which is part of a second embodiment of an electrode device constructed in accordance with the principles of the present invention.
Figure 4:
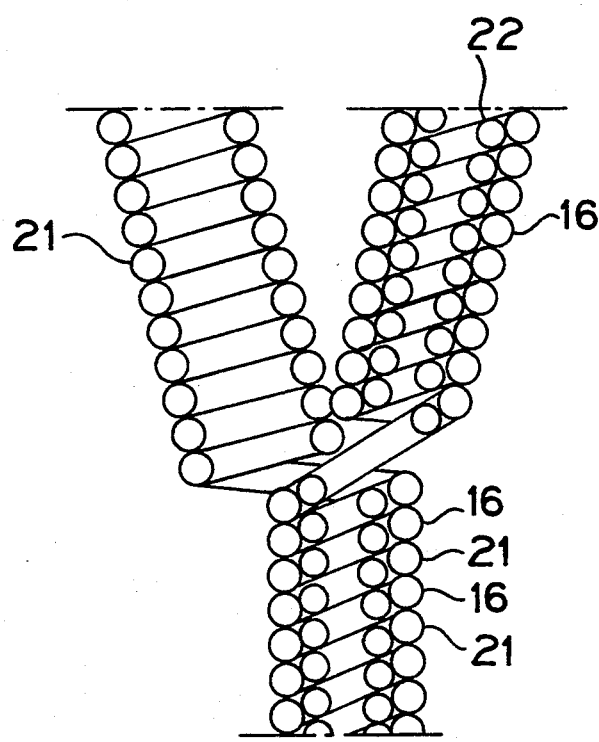
FIG. 4 illustrates a coupling of two electrode conductors in the adapter devices according to FIG. 3.

FIG. 3 illustrates an adapter device 12 which can constitute a detachable part of an electrode device. The adapter device 12 has a connection contact jack 13 at its proximal end, intended for connection to a stimulation pulse generator (not shown) such as a defibrillator. An electrode catheter 17 with a symmetrical lead 6 divide the electrode catheter 17 into two branches 18 and 19. A first contact fixture 14 and a second contact fixture 15 are disposed at the distal ends of the respective branches 18 and 19. A first coiled electrode conductor 16 connects the connection contact 13 to the first contact fixture 14. A second coiled electrode conductor 21 is provided inside the lead 18, and the second electrode conductor 21 is connected to the first electrode conductor 16 in a contact area 20. The second electrode conductor 21 is connected to the second contact fixture 15, thereby connecting the second contact fixture 15 to the connection contact 13 and to the first contact fixture 14. Construction of the connection itself is described in greater detail in conjunction with FIG. 4 below. For example, the electrode device 1 in FIG. 1 can be connected to the contact fixture 14, and a second electrode device, with a transvenous electrode catheter, can be connected to the second contact fixture 15. Such an electrode device (but without the inventive conductor connections) is described in U.S. Pat. No. 4,662,377. A defibrillator pulse, generated by the pulse generator and emitted from a third electrode device across the heart, returns to the pulse generator via the electrode device 1 and the second electrode device. The number of couplings to the pulse generator for returning stimulation pulses is thereby minimized to only one. If the second electrode device and the third electrode device are devised as a single electrode device with two defibrillation electrode arranged along the same transvenous electrode catheter and electrically separated from one another, as taught by the aforementioned U.S. Pat. No. 4,662,377, the total number of connections to the defibrillator can be reduced to only one. The adapter device 12 contains a third conductor 22 which is electrically separated from the other conductors 16 and 21 and which runs from the connection contact 13 to the second contact fixture 15 to electrically couple the defibrillator to the third defibrillator electrode. FIG. 4 shows that the third conductor 22 is coiled into a smaller diameter than the first conductor 16 and provided inside the electrode catheter 17 in such a way that it runs in the channel formed by the coiled first conductor 16. The electrode device can also be devised in the above-described way without a detachable adapter part.

FIG. 4 shows a construction for a coupling of the two electrode conductors 16 and 21. In this instance, the two electrode conductors 16 and 21 are intertwined over a given distance. In the same way as in FIG. 2, the spring force helps to make the coupling mechanically safe and stable while simultaneously assuring a good electrical coupling.

It is possible to devise the coupling between the conductors in FIG. 1 in the way described in FIG. 4 and the coupling of the conductors in FIG. 3 in the way described in FIG. 2.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical electrode arrangement for stimulating living tissue with electrical pulses comprising;
   at least two coiled conductors adapted for in vivo delivery of electrical energy to tissue, said coiled conductors each having a plurality of flights and each conductor exhibiting a spring force due to its coiled structure; and a contact area wherein said coiled conductors are electrically and mechanically interconnected, said flights of said conductors in said contact area being engaged with each other with said spring force of said conductors exclusively forming and maintaining the electrical and mechanical interconnection of said conductors.

2. An electrode arrangement as claimed in claim 1 wherein said coiled conductors are arranged to form a defibrillation electrode, said defibrillation electrode including an electrode carrier on which at least one of said coiled conductors is arranged in a predetermined pattern, said at least one coiled conductor forming an electrode surface through which said electrical energy is transmitted to said tissue, and said defibrillation electrode further comprising an electrode catheter containing a second of said coiled conductors.

3. An electrode arrangement as claimed in claim 2 further comprising a third coiled conductor arranged on said electrode carrier and forming said predetermined pattern in combination with said at least one coiled conductor, said at least one coiled conductor and said a third conductor being electrically interconnected in at least one further contact area, said further contact area being remote from said contact area.

4. An electrode arrangement as claimed in claim 1 further comprising an electrode catheter connected to a symmetrical branched lead, one conductor of said coiled conductors being disposed inside said lead in a first branch and a second conductor of said coiled conductors being disposed inside said electrode catheter in a second branch.

5. An electrode arrangement as claimed in claim 1 comprising a detachable adapter element having an electrode catheter with a contact jack disposed at a first end, and a symmetrical lead with two branches at an opposite second end, each branch of said symmetrical lead terminating in a contact socket, with one conductor of said coiled conductors being disposed inside said symmetrical lead and a second conductor of said coiled conductors being disposed inside said catheter.

6. An electrode arrangement as claimed in claim 1 wherein each of said coiled conductors has the same coiled diameter.

* * * * *